Figure 1A:
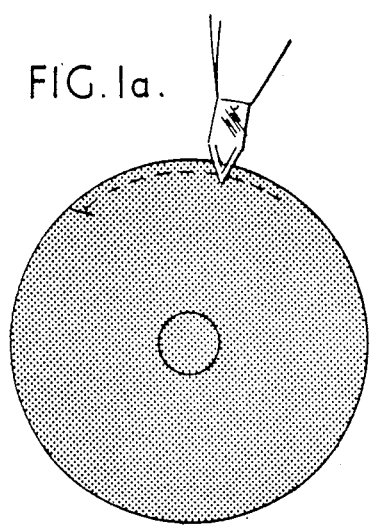

United States Patent [19]

Choyce

[11] Patent Number: 4,655,774

[45] Date of Patent: Apr. 7, 1987

[54] INTRA-CORNEAL IMPLANT FOR CORRECTION OF ANIRIDIA

[76] Inventor: D. Peter Choyce, 9 Drake Road, Westcliff on Sea, Essex SS0 8LR, United Kingdom

[21] Appl. No.: 841,264

[22] Filed: Mar. 19, 1986

[30] Foreign Application Priority Data

Jan. 3, 1986 [GB] United Kingdom ............... 8600079

[51] Int. Cl.⁴ .............................................. A61F 2/14
[52] U.S. Cl. ...................................................... 623/5
[58] Field of Search ................... 623/5, 4, 6; 351/160, 351/162

[56] References Cited

U.S. PATENT DOCUMENTS 3,034,403 5/1962 Neefe ............................. 351/160 X
3,507,566 4/1970 Knapp ................................ 351/160

FOREIGN PATENT DOCUMENTS 2081469 2/1982 United Kingdom .................... 623/6

Primary Examiner—Ronald L. Frinks
Attorney, Agent, or Firm—Hugh D. Jaeger

[57] ABSTRACT

The invention relates to an implant intended to act in place of an iris and comprises an opaque part-spherical annulus of an autoclavable plastics material which is inserted between the layers of the cornea.

The central clear portion of the implant may be an open aperture or may include a lens to correct for defects in eyesight.

3 Claims, 11 Drawing Figures

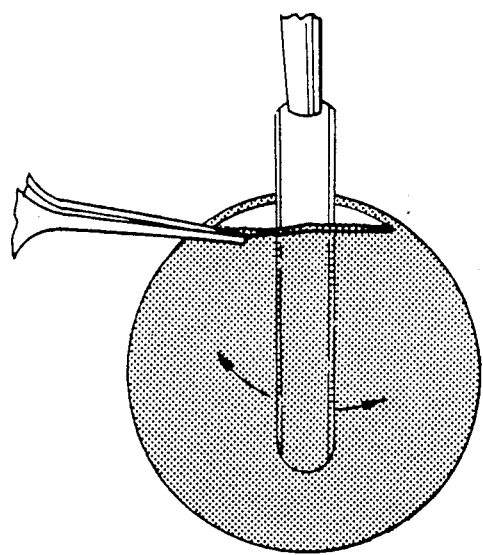
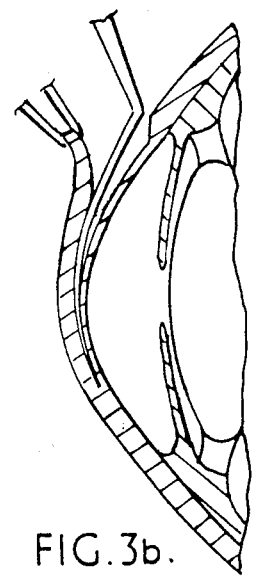
FIG. 3a.  FIG. 3b.
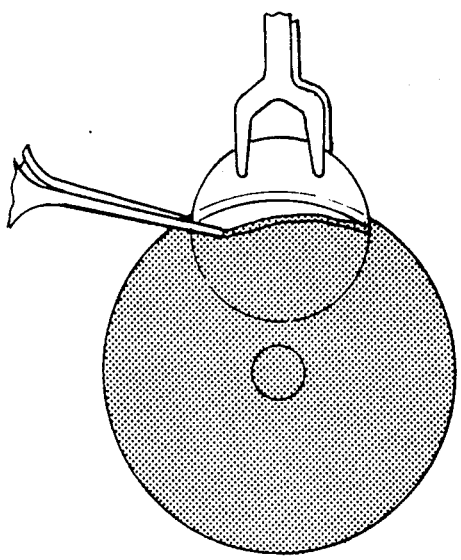
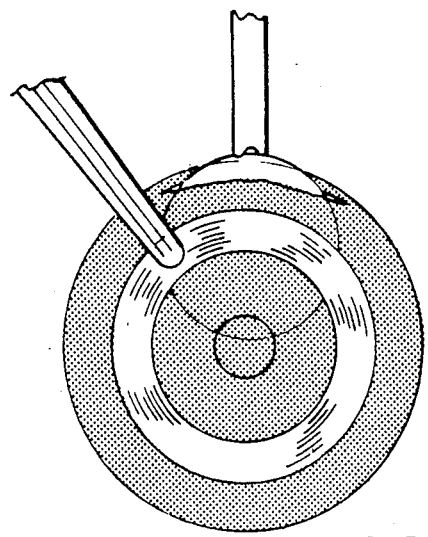
FIG. 4.  FIG. 5.

INTRA-CORNEAL IMPLANT FOR CORRECTION OF ANIRIDIA

The present invention relates to an intra-corneal implant.

Intra-corneal implantation has been used recently to correct such deficiencies as myopia, and hypermetropia and astigmatism. This is described in GB-A-NO. 2,081,469. The intra-corneal inlays mentioned in the latter patent are for correcting defects in eyesight which can alternatively be corrected by the uses of spectacle lenses, contact lenses or intraocular lenses.

The present invention is a development of that in the latter application and is concerned with the treatment of eyes having no iris, a condition referred to as aniridia. This problem is one which may be present at birth, or acquired as the result of injury or disease. When the eye has no iris, the patient will suffer from continual glare and focussing is impaired. Albinism is another condition associated with glare because of deficient iris pigment.

It has been proposed to use an anterior chamber implant, or alternatively a kerato-prosthesis, to act as an artificial iris and artificial lens. This implantation requires a major intrusion into the eye and entails a prolonged recovery period for the patient.

According to the present invention, there is provided an intra-corneal implant which comprises an opaque disc having a generally part spherical surface and a central clear portion, the disc being formed of a clinically inert, autoclavable thermoplastic material.

The plastics material is preferably selected from the group comprising polysulphones, polyethersulphones and polyarylsulphones.

Because the implants are autoclavable, they may be sterilised with ease, thus reducing the cost of the implants and simplifying their use by the surgeon.

The preferred plastics material have the required strength to enable their insertion into a pocket in the cornea, while they retain sufficient flexibility to conform to the shape of the eye.

A further advantage of an intra-corneal iris implant as opposed to an anterior chamber implant is that it can reduce astigmatism caused by deformation of the cornea, this being a problem frequently encountered in albino patients.

The central clear portion may be constituted by an aperature in the opaque plastics material but alternatively it is possible, if desired, to combine such an iris corneal implant with a lens for correcting eyesight defects by incorporating the lens into the central portion of the opaque iris.

It is an important advantage of the preferred plastics materials that even a thin layer can, by the addition of suitable pigments, be made sufficiently opaque to act as an iris. This reduces the obstruction presented by the implant. The plastics materials also retain a certain degree of permeablility which assists in circulation of fluids between the layers of the cornea.

A still further advantage stems from the low density of the implants which reduces their mass and minimises the danger which can be caused by physical shock.

Figure 1B:
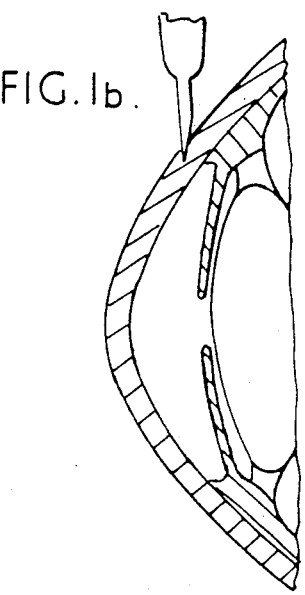
Figure 2A:
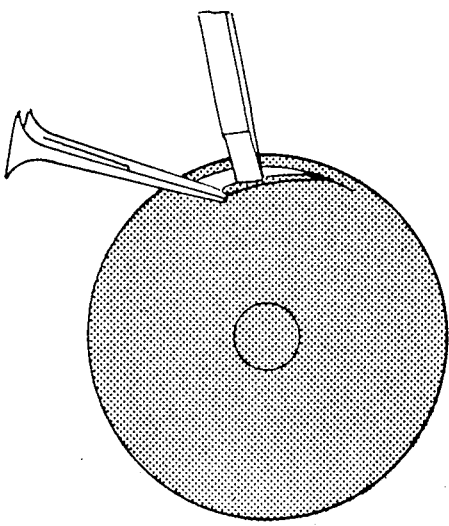
Figure 2B:
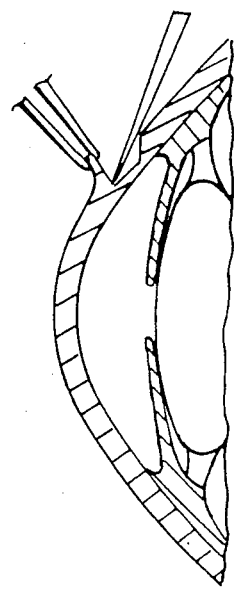
Figure 6A:
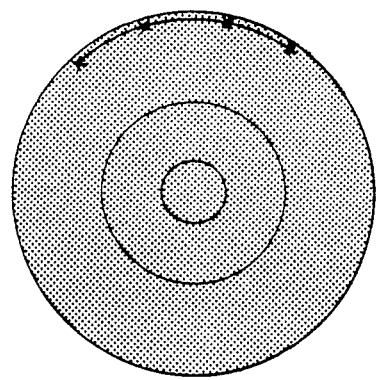
Figure 6B:
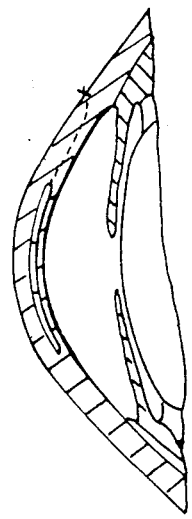
Figure 7:
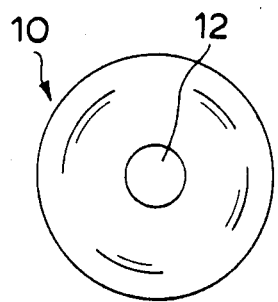

The invention will now be described further, by way of example, with reference to the accompanying drawings, in which:

FIGS. 1a and 1b are a front view and a section, respectively, of the first stage of the operation, FIGS. 2a and 2b are a front view and a sectional view, respectively, showing the second stage of the insertion operation, FIGS. 3a and 3b are a front view and a sectional view, respectively, of a third stage of the insertion operation, FIGS. 4 and 5 show front views during a fourth and the fifth stage of the operation, FIGS. 6a and 6b are a front view and a sectional view, respectively, of the eye after the operation has been completed, and FIG. 7 shows a front view of an intra-corneal iris implant.

The implant 10 shows in FIG. 7 is in the form of a segment of a sphere and is opaque except for a central aperture 12 which is either an open hole or is occupied by a transparent correcting lens.

The implant is made of an autoclavable plastics material which may be a polysulphone, such as UDEL manufactured by Union Carbide Corporation, a polyethersulphone, such as Victrex manufactured by ICI or a polyarylsulphone. Where the implant acts also as a correcting lens, the central part may be made from the same material. The plastics materials given above are naturally clear but can be rendered opaque by means of a biocompatible pigment which colours the material to match the colour of the natural iris.

FIGS. 1 to 6 illustrate an eye operation for the insertion of an intra-corneal implant. The method of insertion applies equally to a correcting lens or an artificial iris but in the interest of clarity the operation illustrated is for the insertion of a transparent lens.

In FIGS. 1a and 1b, an incision is made in the upper layer of the cornea using a diamond tipped cutting tool. As can be seen from FIG. 1b, the incision is made with the tool lying at angle of 45° to the surface of the cornea. It is preferable that a guide stop be formed on the cutting tool in order to prevent excessive penetration of the blade into the cornea since it is desirable not to penetrate the inner membrane of the cornea, known as Descemet's membrane. This incision can alternatively be made vertically with respect to the surface of the cornea.

Once the incision with the sharp diamond tipped blade has been made, a knife with a wider tip is used in a manner shown in FIG. 2 to raise a small flap from the upper layer of the cornea while still holding the cutting blade at 45° to the surface in the manner shown in FIG. 2b.

After a small flap has been raised, it is necessary to form a hollow pocket between the layers of the cornea and this is achieved by inserting a curved instrument with a blunt front end through the incision and the raised flap. This is shown in FIGS. 3a and 3b. The instrument is not fully inserted into the cornea but only to a sufficient extent to form a pocket centred over the pupil of sufficient size to receive the implant.

Once the pocket has been formed, the implant is introduced into the pocket using a forked instrument designed for this purpose (see FIG. 4) and subsequently, using a fine rod formed with a notch in its end surface, the implant is prodded into position (see FIG. 5).

To assist in centering the implant on the pupil, it is desirable to use an instrument such as shown in FIG. 5 which can readily be positioned in a manner concentric with the ring of the sclera. The latter instrument is merely laid over the eye and serves exclusively to assist in visual alignment.

In the final step of the operation, the flap of cornea is sutured using four stitches as shown in FIG. 6.

I claim:

1. An intra-corneal implant for correction of aniridia which comprises an opaque disc having a part spherical surface and a central clear portion, the disc being formed of a clinically inert, autoclavable thermoplastic material selected from the group comprising polysulphones, polyethersulphones and polyarylsulphones.

2. An intra-corneal implant according to claim 1 wherein the central clear portion of the implant is formed by an aperture in the disc.

3. An intra-corneal implant according to claim 1 wherein the clear central portion is formed by a transparent correcting lens.

* * * * *